United States Patent [19]

Harvey et al.

[11] Patent Number: 4,599,436

[45] Date of Patent: Jul. 8, 1986

[54] FORMS OF AUROTHIOMALATE HAVING THERAPEUTIC ADVANTAGE

[75] Inventors: Debra A. Harvey, Hamilton; Walter F. Kean, Dundas; Colin J. L. Lock, Burlington, all of Canada

[73] Assignee: Canadian Patents and Development Limited, Ottawa, Canada

[21] Appl. No.: 479,746

[22] Filed: Mar. 28, 1983

[51] Int. Cl.[4] .............................................. C07F 1/12
[52] U.S. Cl. ...................................... 556/114; 556/113
[58] Field of Search ................. 260/430; 556/113, 114

[56] References Cited

U.S. PATENT DOCUMENTS

| 1,517,002 | 11/1924 | Hahl et al. | 260/430 |
|---|---|---|---|
| 1,683,104 | 9/1928 | Schoeller et al. | 260/430 |
| 1,994,213 | 3/1935 | Delépine | 260/430 |
| 2,049,198 | 7/1936 | Delange | 260/430 |
| 2,352,124 | 6/1944 | Sabin et al. | 260/430 X |
| 2,509,200 | 5/1950 | Moore et al. | 260/430 |
| 2,880,222 | 3/1959 | Friedheim | 260/430 |
| 3,718,679 | 2/1973 | McGusty et al. | 260/430 |
| 4,165,380 | 8/1979 | Hill | 260/430 X |
| 4,315,028 | 2/1982 | Scheinberg | 424/290 |

Primary Examiner—Helen M. S. Sneed
Attorney, Agent, or Firm—Alan A. Thomson

[57] ABSTRACT

Sodium aurothiomalate used as a therapeutic agent or as a component in a therapeutic agent is shown to be a mixture of substances, one of which is non-toxic to blood platelets, shows specific spectral absorption visibility and does not demonstrate the usual irregular gold containing particles in platelets. As well as being an improvement on the mixture currently employed, the colorless state of sodium aurothiomalate shows promise as an antithrombitic agent.

5 Claims, 3 Drawing Figures

FORMS OF AUROTHIOMALATE HAVING THERAPEUTIC ADVANTAGE

DESCRIPTION OF THE PRIOR ART

Sodium aurothiomalate has been used in the treatment of rheumatoid arthritis for over thirty years. U.S. Pat. No. 1,994,213 describes a process for the manufacture of sodium aurothiomalate and claims a hydrated salt of sodium aurothiomalate. U.S. Pat. No. 2,352,124 describes the production of calcium aurothiomalate from sodium aurothiomalate, the toxicity of the latter in many cases making it desirable to look for alternatives. The concern with the instability of gold organic compounds in aqueous solutions and with their hygroscopic properties, which mean that the solid compounds are subject to the deleterious effects of atmospheric moisture on storage, led to U.S. Pat. No. 2,509,200 which claims, among other things, the compound monosodium salt of gold thioitamalic acid. U.S. Pat. No. 3,792,165 continues the search of satisfactory gold-containing compounds and describes the production of phosphine or phosphite gold complexes of thiomalic acid having antiarthritic activity. More recently, U.S. Pat. No. 4,165,380 describes bis(sulphide)-gold(1+) salts which have antiarthritic activity, and U.S. Pat. No. 4,330,530 describes compositions of pharmaceutically acceptable gold salts, including sodium thiomalate, and organophosphonates.

In U.S. Pat. No. 1,648,213, compositions of aurosodium thiosulphate solutions which are colourless, clear solutions remaining clear on sterilising are described. Hence, it would appear that, with a continuing demand for a composition of matter that can be used to treat arthritis and that also has low toxicity, a reexamination of some of the earlier compositions is appropriate.

SUMMARY OF THE INVENTION

This invention concerns a pure, colourless form of sodium aurothiomalate having the following characteristics:
spectral absorption patterns shown in FIG. 1,
lack of platelet toxicity,
inability to provoke the appearance of gold-containing particles within platelets on treatment thereof with the said colourless form of sodium aurothiomalate, in amounts which for the coloured form of sodium aurothiomalate do cause the appearance of gold-containing particles.

The pure, colourless form of sodium aurothiomalate is made by a method of manufacture comprising: (a) forming an opalescent mixture of with sodium aurothiomalate with a lower alkanol having no more than four carbon atoms, for example, methanol; (b) adding water until the opalescence of solution disappears and an essentially colourless solution is produced; (c) separating the the mixture from a yellow gummy residue, the residue being discarded to yield an aqueous solution of a pure, essentially colourless form of sodium aurothiomalate. Step (c) may be followed by evaporation to dryness, preferably under vacuum, to yield a pure, essentially colourless form of sodium aurothiomalate.

The above form of sodium aurothiomalate, ready for injection, dissolved or dispersed in an injectable liquid medium such as sterile water.

DESCRIPTION OF THE INVENTION

Sodium aurothiomalate has been used in the treatment of rheumatoid arthritis for approximately thirty years. It is efficacious in approximately 70% of patients with rheumatoid arthritis but it has a high toxicity rate of 30-50% and, therefore, has to be administered using guidelines for strict drug usage. Some of the potential side effects are skin rash, proteinuria, mouth ulcers, thrombocytopenia (low platelet counts) and bone marrow depression. Sodium aurothiomalate is described in the literature as the chemical formula $C_4H_3AuNa_2O_4S$ with a molecular weight of 390.12 (see Martindale, The Extra Pharmacopoeia, 27th Edition, p. 896, The Pharmaceutical Press, London, 1977). Because of the known chemical properties of gold, it is unlikely that the drug exists as a monomeric species as depicted above but probably exists in a polymeric form in which gold and sulphur molecules are linked in a chain of, at present, unknown length. As currently marketed, sodium aurothiomalate is a yellow solution. However, when it is prepared from a solid (powder form) it is a colourless solution. The colourless solution becomes yellow during the standard sterilization procedures employed by the marketing companies. There are physical, chemical and biological differences between the colourless and the yellow solutions. There are (a) spectroscopic light absorption differences, (b) nuclear magnetic resonance spectroscopy differences, and (c) the yellow solution contains particulate gold-containing particles which cause human blood platelet aggregation, whereas the colourless compound has no effect on platelets.

We believed that solid sodium aurothiomalate was one compound and that a freshly prepared solution also contained only one component, which then underwent thermal or photodecomposition into other (yellow) components. However, we now believe that the original solid and solution contain at least two components and that the reaction may be represented by:

Original solid or solution

-continued
Original solid or solution

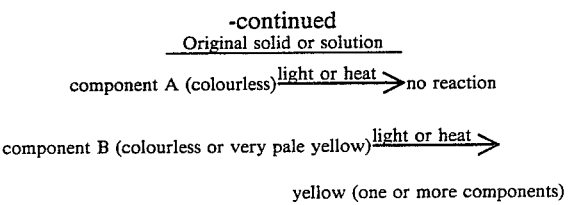

yellow (one or more components)

EXAMPLE 1

Separation of the Forms of Sodium Aurothiomalate 0.25 g of sodium aurothiomalate was shaken with 10 ml of methanol and then 5–10 ml of sterile water added until the opalescense in the solution disappears. A yellow gum is produced and sticks to the bottom and sides of the tube. The colourless solution is decanted off and evaporated to dryness under vacuum. The yellow gum can also be solidified by drying under vacuum. The product from the colourless solution is stable to heat and light and non-toxic to platelets; the solidified yellow gum (which gives a very pale yellow solid) is sensitive to heat and light and is toxic to platelets.

EXAMPLE 2

Figure 1:
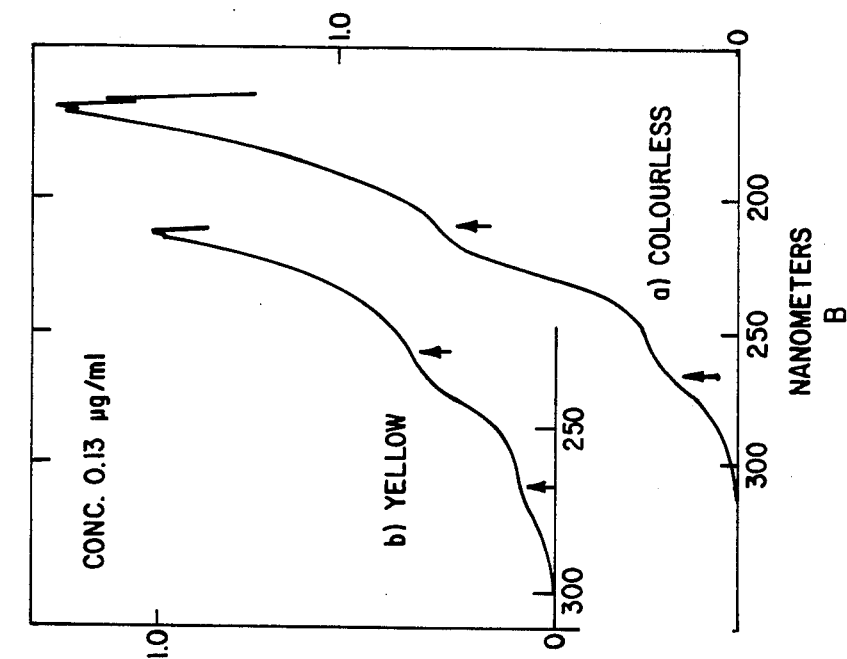
FIG. 1A shows spectral absorption patterns, in the visible light range (350–450 nm), of, (a) the colourless and (b) the yellow, forms of sodium aurothiomalate.
FIG. 1B shows spectral absorption patterns in the ultraviolet range (180–350 nm). In both FIGS. 1A and 1B the bottom curves read on to the right hand ordinate scale. The optical density is displayed on the ordinate axis.
Figure 1:
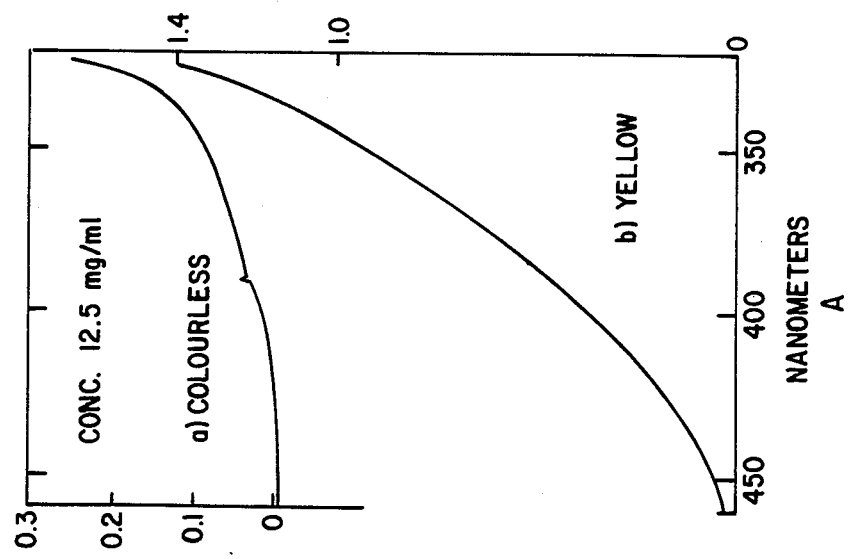

Characterization of the Two Forms of Sodium Aurothiomalate (A) Spectral Absorption Patterns Differences were found in the spectral absorption patterns of the colourless and yellow forms of sodium aurothiomalate (see FIG. 1) as measured in aqueous solutions in 1 cm. cells with use of a Pye-Unicam SP8-100 (trademark) spectrophotometer. Not only were differences found in the visible spectrum (FIG. 1A) but there were also demonstrable differences in the ultraviolet range (FIG. 1B).

(B) Platelet Aggregation Studies

Figure 2:
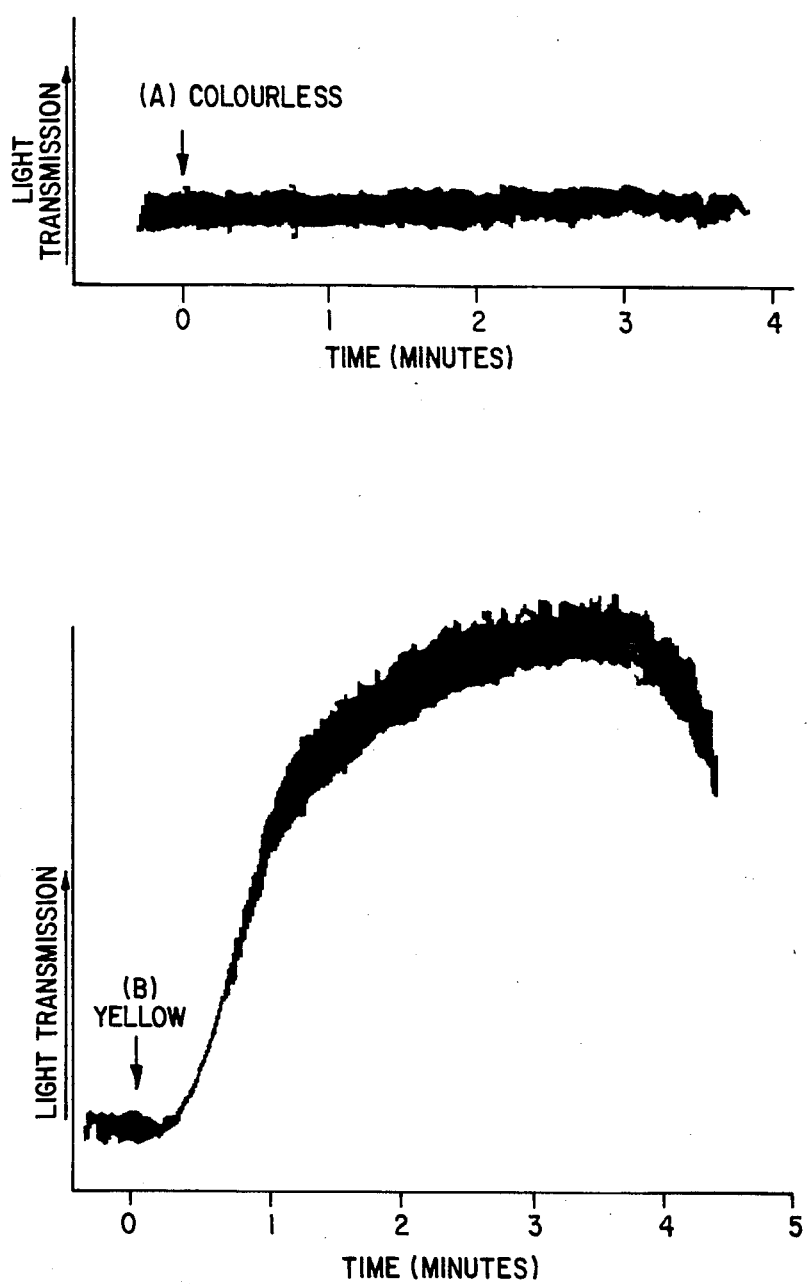
FIG. 2 shows the effect of the addition of, (a) the colourless and (b) the yellow, forms of sodium aurothiomalate to washed human platelets. The degree of light transmission is taken as a measure of platelet aggregation, and varies from 0% for platelets in suspension (complete opacity) to approximately 100% for complete platelet clumping and aggregation (100% is a reference standard of sterile water).

Differences were also found in platelet toxicity as measured by the relative ability of the compounds to cause platelet aggregation (see FIG. 2). The procedure employed to obtain platelets was as follows: 129 ml of blood was obtained by antecubital vein puncture from volunteers. Volunteers were selected who were on no medications and had taken no medication for two weeks. The blood was immediately transferred in equal volumes to 3 plastic centrifuge tubes (5 ml), each containing 7 ml of acid-citrate-dextrose (ACD) anticoagulant solution. The whole blood-ACD mixture was gently but rapidly mixed to prevent clotting. The suspension was then centrifuged at 37° C. in an R.C.3 Sorval centrifuge at 1200 g for 3 minutes. The platelet-poor plasma was discarded and the platelets were suspended in Tyrodes solution containing 0.35% albumin. Apyrase prepared according to Molnar and Lorand, with a nucleotidase activity of 5.3 units of adenosine diphosphatase/mg and 4.2 units of adenosine triphosphatase/mg was included in the Tyrodes albumin solution at a concentration of 10 μl/ml. Platelets were incubated in this first washing solution of Tyrodes albumin with 2 μCi of $^{14}C$-serotonin and 200 μCi of disodium chromate/mg for 30 minutes. This first washing solution was then centrifuged at 1200 g for 10 minutes, the supernatant discarded and the platelets resuspended in Tyrodes albumin solution (second washing solution) for 10 minutes. The second washing solution of platelets was centrifuged at 1200 g for 10 minutes and the supernatant discarded. The platelets were suspended in a final suspension of Tyrodes albumin and the platelet count adjusted to 500,000/mm³. The platelet suspensions were stored at 37° C. in a water bath prior to use.

Platelet aggregation was studied by a modification of a turbidimetric method. Light transmission of 1 ml suspensions of washed platelets was measured on a Payton Aggregation Module and recorded on a Rikadenki Pen Recorder. Platelet shape change and aggregation were recorded following the interaction with test compounds (e.g. gold complexes) and aggregating agents (e.g. ADP).

The yellow solution of gold sodium thiomalate ($1.3 \times 10^{-3}$–$6.4 \times 10^{-3}$M as elemental gold) added to washed human platelets resulted in shape change within 30 seconds followed by platelet aggregation (see FIG. 2) and release of internal granule contents as measured by $^{14}C$-serotonin radioactivity. De-aggregation of platelets usually occurred within 2 to 4 minutes and is seen as a decline in light transmission after about 4 minutes in FIG. 2. Due to the wide biological variability demonstrated by the platelets, $^{14}C$-serotonin release values could not be compared between individual samples obtained from different volunteers. However, within samples, $^{14}C$-serotonin release values, paralleled the increase in concentration of the yellow solution of gold thiomalate. The usual values for $^{14}C$-serotonin release were between 5% and 20% for the elemental gold concentration range of, $1.3 \times 10^{-3}$–$6.4 \times 10^{-3}$M. Platelet lysis as measured by $^{51}Cr$ release did not occur within this concentration range of elemental gold. Platelet aggregation was not observed where gold concentrations of the yellow solution of sodium aurothiomalate were less than $1.3 \times 10^{-3}$M.

When a range of concentration of the colourless solution of gold sodium thiomalate ($1.8 \times 10^{-5}$–$6.4 \times 10^{-3}$M) was added to washed human platelets, no reactivity of the platelets was observed, as measured by a lack of platelet aggregation and of $^{14}C$-serotonin release.

Similarly, gold thioglucose and gold sodium thiosulphate in equimolar concentrations of elemental gold ($1.8 \times 10^{-5}$–$6.4 \times 10^{-3}$M) and disodium thiomalate in equimolar concentrations of thiomalate to the concentrations of thiomalate in sodium aurothiomalate solutions containing $1.8 \times 10^{-5}$–$6.4 \times 10^{-3}$M of elemental gold did not cause platelet aggregation nor release of internal granules.

It is also worth noting that the lack of ability to cause platelet aggregation, is linked to the inability of the purified compound to provide the appearance of gold-containing particles within platelets which have been subjected to the purified compound in amounts which for the coloured form of sodium aurothiomalate do cause the appearance of gold-containing particles.

Figure 3:
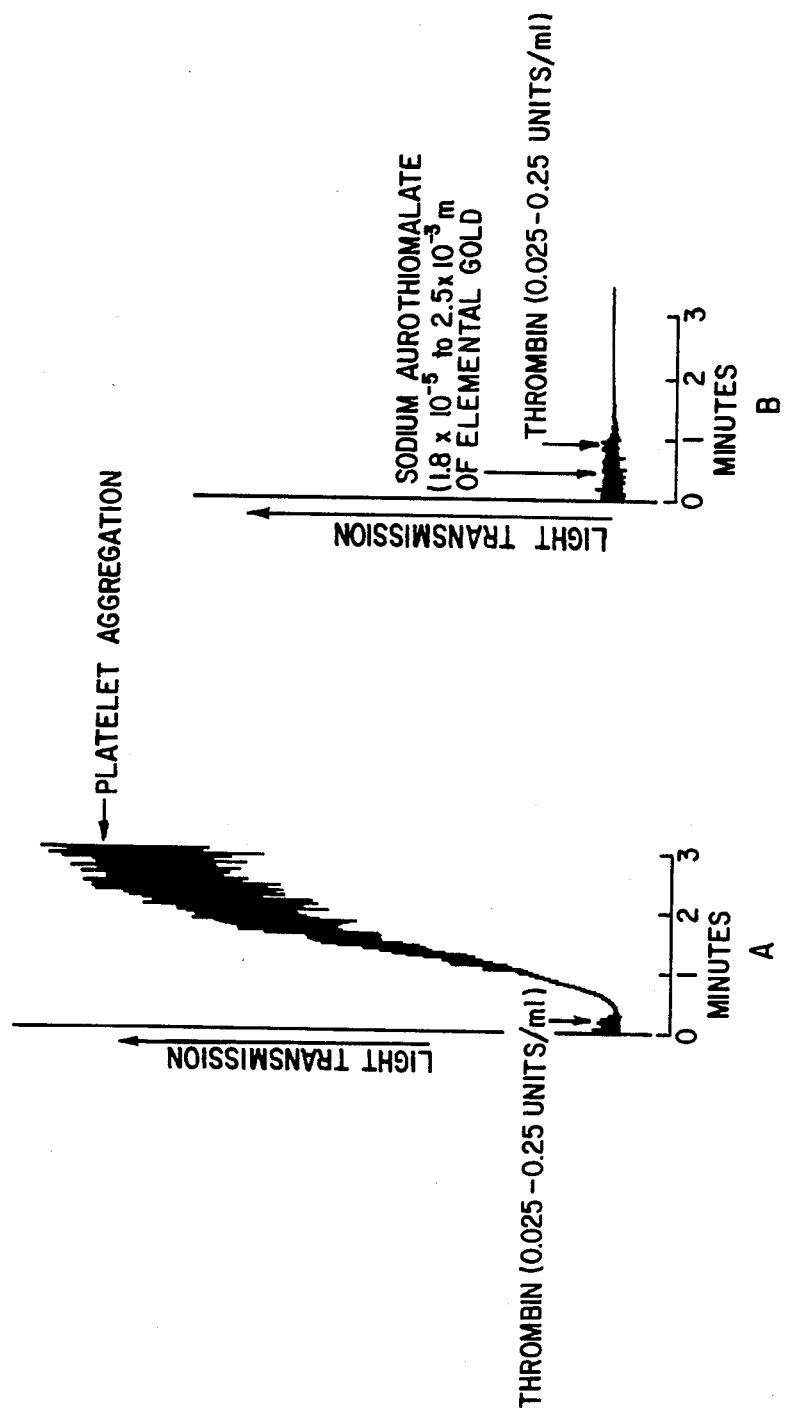
FIG. 3 shows that sodium aurothiomalate, normally at lower concentrations than those employed in the experiments illustrated by FIG. 2, added before thrombin to washed human platelets, inhibits the normal action of thrombin upon such washed human platelets, of platelet aggregation and serotonin release. The degree of light transmission is measured as in FIG. 2.

Initial in vitro studies demonstrated that both the colourless and yellow forms of gold sodium-thiomalate inhibited the action of thrombin on washed human platelets (see FIG. 3). 0.025 to 0.25 units/ml of thrombin were added to washed human platelets. This induced platelet aggregation and was accompanied by 35–90% release of $^{14}C$-serotonin which paralleled platelet aggregation. Prior addition of either colourless or yellow sodium aurothiomalate in a concentration range of $1.8 \times 10^{-5}$–$2.5 \times 10^{-3}$M, measured as elemental gold, blocks the aggregation of washed human platelets by thrombin and also the release of $^{14}C$-serotonin. Both the colourless and yellow forms of gold sodium thiomalate prolong the thrombin clotting time of platelet rich plasma and platelet-poor plasma in a similar manner. An example of the action of the yellow form of gold sodium thiomalate on platelet rich plasma and platelet-poor plasma is shown in Table I.

In view of these results, in vivo experiments were undertaken to investigate the effects of yellow gold sodium thiomalate on experimentally induced thrombosis in rabbits.

This invention includes a method of treating individuals prone to thrombosis comprising administering parenterally the colourless form of sodium aurothiomalate in amounts sufficient to inhibit the formation of thromboses.

In order to study the effect of gold compounds on the action of thrombin in vivo, the weight of thrombus formation was studied in an experimental model of intra aortic thrombosis induced by an indwelling aortic catheter method. The experiment was carried out over 12 days. Male New Zealand rabbits (2.5–3.5 kilograms) were given daily injections of drug on days 1 to 5 and the indwelling aortic catheter was surgically inserted on day 8. The rabbits were sacrificed on day 12. In order to obtain a relative uniformity of serum gold by day 8 (i.e. day of catheter insertion) for each gold complex administered, pilot dosage studies with 8 rabbits in each group were undertaken. Using equimolar concentration of the gold compounds at 0.13M as elemental gold in 0.5 ml of sterile water given intramuscularly daily from day 1 to 5, the following mean serum gold levels ($\pm$SEM) could be achieved: gold sodium thiomalate treated, $1.0 \times 10^{-4} M \pm 6.7 \times 10^{-6} M$; gold thioglucose treated $1.1 \times 10^{-4} M \pm 4.7 \times 10^{-6} M$ gold sodium thiosulphate treated $1.6 \times 10^{-4} M \pm 5.6 \times 10^{-6} M$. Control animals were given 0.5 ml of sterile water intramuscularly daily for 5 days. Disodium thiomalate was administered as 0.13M thiomalate in 0.5 ml of sterile water.

Table 2 shows that there is a significant reduction in thrombus weight in animals treated with yellow gold sodium thiomalate compared to controls and other test compounds. In view of the advantages of the colourless form over the yellow form, outlined above, methods of treating individuals prone to thrombosis would preferably employ the colourless form of sodium aurothiomalate in amounts sufficient to inhibit the production of thromboses.

TABLE 1

THE EFFECT OF GOLD SODIUM THIOMALATE ON THE THROMBIN CLOTTING TIME IN VITRO

| GOLD SODIUM THIOMALATE (Moles of Elemental Gold) | THROMBIN TIME | |
|---|---|---|
| | PLATELET POOR PLASMA (Seconds $\pm$ SEM) | PLATELET RICH PLASMA (Seconds $\pm$ SEM) |
| 0 | 17.7 $\pm$ 0.4 | 16.5 $\pm$ 0.2 |
| $2.1 \times 10^{-4}$ | 18.7 $\pm$ 0.1 | 17.4 $\pm$ 0.3 |
| $4.2 \times 10^{-4}$ | 19.6 $\pm$ 0.2 | 18.3 $\pm$ 0.6 |
| $1.0 \times 10^{-3}$ | 24.6 $\pm$ 0.4 | 22.2 $\pm$ 0.7 |
| $2.1 \times 10^{-3}$ | 33.2 $\pm$ 0.9 | 30.2 $\pm$ 0.9 |
| $4.2 \times 10^{-3}$ | 60.7 $\pm$ 1.7 | 51.7 $\pm$ 1.4 |
| $2.1 \times 10^{-2}$ | $\infty$ | $\infty$ |

Representative experiment. Each thrombin time sampled 5 times
S.E.M.—Standard error of the mean
$\infty$ = Infinity

TABLE 2

THE WEIGHT (mg) OF EXPERIMENTALLY INDUCED THROMBUS FROM RABBITS WITH INDWELLING AORTIC CATHETERS

| | TREATMENT | | | | |
|---|---|---|---|---|---|
| | $H_2O$ | GOLD SODIUM THIOMALATE | GOLD THIOGLUCOSE | GOLD THIOSULPHATE | SODIUM THIOMALATE |
| N | 19 | 12 | 5 | 5 | 4 |
| MEAN THROMBUS WEIGHT. (mg) | 31.01 | 14.79 | 23.60 | 20.60 | 23.40 |
| S.D. | 16.03 | 11.09 | 10.10 | 7.19 | 4.22 |
| S.E.M. | 4.24 | 3.32 | 2.00 | 2.00 | 1.73 |
| | In view of skewed data due to biological variation, statistical analysis was calculated using log thrombus weight values. | | | | |
| ANTILOG OF MEAN VALUE OF SUM OF LOG THROMBUS WEIGHTS | 26.92 | 11.14 | 21.95 | 19.74 | 23.13 |
| 95% CONFIDENCE LIMITS | 15.03–48.03 | 4.88–25.46 | 14.37–33.55 | 14.40–27.09 | 19.43–33.55 |

Statistical comparison of antilogs of mean value of sum of log thrombus weights were calculated by one way analysis of variance and Dunnett's test. The thrombus weight of gold sodium thiomalate treated animals was significantly less than all other treatment groups. (p = 0.035)
N = Number of rabbits in each category
mg = Milligrams
SD = Standard deviation
S.E.M. = Standard error of the mean

We claim:

1. A pure colourless form of sodium aurothiomalate having the following characteristics:
   an optical density below about 0.3 throughout the visible light range of 350 to 450 nm when in aqueous solution at a concentration of about 12.5 mg/ml,
   lack of platelet toxicity as measured by platelet aggregation and concomitant serotonin release,
   inability to provoke the appearance of gold-containing particles within platelets on treatment thereof with the said colourless form of sodium aurothiomalate, in amounts which, for the coloured form of sodium aurothiomalate, do cause the appearance of gold-containing particles.

2. The compound of claim 1 dissolved or dispersed in an injectable liquid medium.

3. A method of manufacture of a solution of the compound of claim 1 comprising:
   (a) forming an opalescent mixture of sodium aurothiomalate with a lower alkanol, said lower alkanol containing 1 to 4 carbon atoms;

(b) adding water until opalescence in the solution disappears and an essentially colourless solution is produced;
(c) separating the solution from a yellow gummy residue, the residue being discarded, to yield an aqueous solution of a pure, essentially colourless form of sodium aurothiomalate.

4. The method of claim 3 wheren the lower alkanol employed in step (a) is methanol.

5. The method of claim 3 followed by an additional step (d) comprising evaporating the solution separated in step (c) to dryness to yield the pure, colourless form of sodium aurothiomalate.

* * * * *